United States Patent
Rao

[11] Patent Number: 5,919,994
[45] Date of Patent: Jul. 6, 1999

[54] CATALYTIC HALOGENATED HYDROCARBON PROCESSING AND RUTHENIUM CATALYSTS FOR USE THEREIN

[75] Inventor: Velliyur Nott Mallikarjuna Rao, Wilmington, Del.

[73] Assignee: E. I. du Pont de Nemours and Company, Wilmington, Del.

[21] Appl. No.: 08/875,470

[22] PCT Filed: Nov. 26, 1996

[86] PCT No.: PCT/US96/18952

§ 371 Date: Jul. 28, 1997

§ 102(e) Date: Jul. 28, 1997

[87] PCT Pub. No.: WO97/19750

PCT Pub. Date: Jun. 5, 1997

Related U.S. Application Data

[60] Provisional application No. 60/007,702, Nov. 29, 1995.

[51] Int. Cl.$^6$ .......................... C07C 17/093; C07C 19/01
[52] U.S. Cl. .......................... 570/176; 570/177; 585/612; 585/733
[58] Field of Search ..................................... 570/170, 176, 570/177, 227; 589/612, 620, 627; 585/629, 733; 208/262.1

[56] References Cited

U.S. PATENT DOCUMENTS

| | | | |
|---|---|---|---|
| 3,505,417 | 4/1970 | Gardner | 260/653.5 |
| 3,636,173 | 1/1972 | Gardner | 260/653.5 |
| 4,760,187 | 7/1988 | Kosak | 564/417 |
| 4,902,838 | 2/1990 | Manzer et al. | 570/151 |
| 5,068,472 | 11/1991 | Webster et al. | 570/157 |
| 5,068,473 | 11/1991 | Kellner et al. | 570/176 |
| 5,171,901 | 12/1992 | Gassen et al. | 570/168 |
| 5,202,510 | 4/1993 | Kellner | 570/176 |
| 5,315,048 | 5/1994 | Van Der Puy et al. | 570/176 |
| 5,430,214 | 7/1995 | Smith et al. | 585/641 |
| 5,559,069 | 9/1996 | Rao et al. | 502/226 |
| 5,561,096 | 10/1996 | Schoebrechts et al. | 502/330 |
| 5,569,797 | 10/1996 | Fu et al. | 570/177 |

FOREIGN PATENT DOCUMENTS

WO 95/05353  2/1995  WIPO .......................... C07C 19/08

*Primary Examiner*—Bekir L. Yildirim

[57] ABSTRACT

Processes for decreasing the chlorine to carbon ratio for halogenated hydrocarbons containing chlorine and from 1 to 6 carbon atoms, in the presence of a catalyst are disclosed. The processes are each characterized by employing a catalyst comprising ruthenium on a support of (i) fluorided alumina, (ii) aluminum fluoride, or (iii) fluorides of Zn, Mg, Ca, Ba, Y, Sm, Eu, and/or Dy. Also disclosed are multiphase catalyst compositions of ruthenium supported on fluorides of Zn, Mg, Ca, Ba, Y, Sm, Eu and/or Dy.

8 Claims, No Drawings

CATALYTIC HALOGENATED HYDROCARBON PROCESSING AND RUTHENIUM CATALYSTS FOR USE THEREIN

This application is a national filing under 35 USC 371 of International Application No. PCT/US96/18952 filed Nov. 26, 1996 claiming priority of U.S. Provisional application Ser. No. 60/007,702 filed Nov. 29, 1995.

FIELD OF THE INVENTION

This invention relates to supported ruthenium compositions and their use, and more particularly to supported ruthenium catalysts and their use for processing halogenated hydrocarbons.

BACKGROUND

A variety of metal catalysts have been proposed for use in processes for dimerizing chlorine-containing fluorocarbons, for dehalogenating halogenated fluorocarbons for hydrogenolyzing halogenated hydrocarbons and for hydrofluorating halogenated hydrocarbons (see e.g., PCT Publication No. WO 95/05353 for dimerization examples and L. E. Manzer et al., Adv. Catal. (39) pp. 329–350 (1993) for examples of the other listed processes). The products of these processes are useful for the preparation of hydrofluorocarbons which can be substituted for chlorofluorocarbons and hydrochlorofluorocarbons which have been used as refrigerants, blowing agents and cleaning agents. Some of the olefinic products are useful as monomers for fluoropolymers. There is an interest in developing economical processes for the preparation of such compounds.

SUMMARY OF THE INVENTION

This invention provides processes for decreasing the chlorine to carbon ratio for halogenated hydrocarbons containing chlorine and from 1 to 6 carbon atoms, in the presence of a catalyst. The processes are each characterized by employing a catalyst comprising ruthenium on a support selected from the group consisting of (i) fluorided alumina, (ii) aluminum fluoride, and (iii) fluorides of at least one metal selected from the group consisting of Zn, Mg, Ca, Ba, Y, Sm, Eu, and Dy (e.g., zinc fluoride, magnesium fluoride, calcium fluoride, barium fluoride, yttrium fluoride, samarium fluoride, europium fluoride and/or dysprosium fluoride).

This invention further provides multiphase catalyst compositions consisting essentially of ruthenium supported on fluorides of at least one element selected from the group consisting of Zn, Mg, Ca, Ba, Y, Sm, Eu and Dy.

DETAILED DESCRIPTION

The catalytic processes of this invention include processes for dimerizing, processes for dehalogenating, processes for hydrogenolyzing, and processes for increasing the fluorine content of chlorinated fluorocarbons (i.e., compounds containing only carbon, chlorine and fluorine) and chlorinated hydrofluorocarbons (i.e., compounds containing only carbon, hydrogen, chlorine and fluorine). The chlorinated fluorocarbons and chlorinated hydrofluorocarbons can contain from 1 to 6 carbon atoms. The processes employ a supported ruthenium catalyst. The support (i.e., carrier) can be fluorided alumina, aluminum fluoride, zinc fluoride, magnesium fluoride, calcium fluoride, barium fluoride, yttrium fluoride, samarium fluoride, europium fluoride and/or dysprosium fluoride. Fluorided alumina and aluminum fluoride can be prepared as described in U.S. Pat. No. 4,902,838. The other metal fluorides as well as aluminum fluoride can be obtained commercially. The ruthenium can be supported on the carrier by techniques well known in the art such as impregnation. The concentration of ruthenium on the support is typically in the range from about 0.01 to 30 weight percent, and is preferably from about 0.5 to 20 weight percent.

Included in this invention is a process for dimerizing saturated compounds having the formula $C_nH_aCl_bF_c$ where n is an integer from 1 to 4, a is an integer from 0 to 1, b is an integer from 2 to 9, c is an integer from 0 to 9, where a+b+c equals 2n+2, and where two chlorines that are removed are on the same carbon atom, by reacting said compound with hydrogen in the vapor phase to produce olefins of the formula $C_{2n}H_{2a}Cl_{2b-4}F_{2c}$; a process for dehalogenating a saturated compound having the formula $C_mH_dCl_eF_f$ where m is an integer from 2 to 6, d is an integer from 0 to 2, e is an integer from 2 to 4, f is an integer from 3 to 12, where d+e+f equals 2m+2, by reacting said compound with hydrogen in the vapor phase to produce olefins of the formula $C_mH_dCl_{e-y}F_{f-y}$, where y is an integer from 1 to 2 when m is an integer from 2 to 3, and y is an integer from 2 to 4 when m is an integer from 4 to 6, provided that a chlorine atom on each of two adjacent carbons or a fluorine and a chlorine atom on two adjacent carbons (but not a fluorine atom on each of two adjacent carbons) are removed; a process for increasing the fluorine content of a saturated or olefinic compound having the formula $C_kH_gCl_hF_i$ where k is an integer from 1 to 6, g is an integer from 0 to 4, h is an integer from 1 to 13, i is an integer from 0 to 13, provided that h is at least 1 when the compound is saturated, by reacting said compound with HF in the vapor phase; and a process for the hydrogenolysis of a compound of the formula $CF_3(CF_2)_pCCl_2(CF_2)_qCF_3$ where p and q are independently 0 or 1, by reacting said compound with hydrogen in the vapor phase.

The dimerization reaction of said compounds of the formula $C_nH_aCl_bF_c$ with hydrogen is typically conducted at a temperature from about 100° C. to 400° C., preferably from about 125° C. to 375° C., and more preferably from about 150° C. to about 300° C. Typically, the contact time is from about 1 to about 100 seconds, preferably from about 5 to about 60 seconds. The mole ratio of hydrogen to $C_nH_aCl_bF_c$ compound(s) ordinarily should be at least about 0.25:1. Typically, the molar ratio of hydrogen to said compounds of the formula $C_nH_aCl_bF_c$ ranges from about 0.5:1 to about 10:1, and is preferably about 0.5:1 to 5:1, and more preferably about 0.5:1 to 2:1. In general, with a given catalyst composition, the higher the temperature and the longer the contact time, the greater is the conversion to dimerized products. The above variables can be balanced, one against the other, so that the formation of dimerized products is maximized.

Examples of halogenated hydrocarbons of the formula $C_nH_aCl_bF_c$ which may be reacted with hydrogen include, $CCl_4$, $CCl_3CClF_2$, $CCl_3CF_3$, $CF_3CCl_2CF_3$, $CCl_3CF_2CF_3$, $CCl_3CF_2CF_2CF_3$ and $CF_3CCl_2CF_2CF_3$. Of note is a catalytic process for producing cis and trans 2,3-dichloro-1,1,1,4,4,4-hexafluorobutene-2 (i.e., F1316mxx or $CF_3CCl\!=\!CClCF_3$) by the reaction of hydrogen with $CCl_3CF_3$. This dimerization reaction is done in the presence of the supported ruthenium catalysts described above and is preferably conducted at about 125° C. to 300° C., more preferably about 150° C. to 250° C.

Also of note is a catalytic process for producing cis and trans 3,4-dichloro-1,1,1,2,2,5,5,6,6,6-decafluorohexene-3 (i.e., F151-10mcxx or $C_2F_5CCl\!=\!CClC_2F_5$). Starting materials include 1,1,1-trichloro-2,2,3,3,3-pentafluoropropane. A catalytic process for producing 2,3-trifluoromethyl-1,1,1,4,4-hexafluorbutene-2 (i.e., F151-12mmtt or $(CF_3)_2C\!=\!C(CF_3)_2$ from 2,2-dichloro-1,1,1,3,3,3-hexafluoropropane is also of note.

The dimerized products which are unsaturated and/or contain chlorine can be further reacted with hydrogen or a fluorinating agent (e.g., HF) in the presence of the same or optionally a second catalyst. Further reacting the dimerized products with hydrogen (optionally using a second catalyst) can produce hydrofluorocarbons. Reaction with a fluorinating agent can produce a hydrofluorocarbon or a perfluorinated alkane.

The catalyst used for the hydrogenation reaction may be the same catalyst used for the dimerization reaction or may be selected from metals known to provide significant hydrogenolysis activity on supports such as alumina, fluorided alumina and carbon. A preferred catalyst contains at least one metal selected from the group consisting of rhenium, cobalt, nickel, ruthenium, rhodium, palladium, osmium, iridium and platinum supported on carbon with an ash content of less than 0.5% by weight. The reaction of the dimerized products and hydrogen can be performed in liquid or vapor-phase using well-known chemical engineering practice, which includes continuous, semi-continuous or batch operations. The hydrogenolysis process is achieved at atmospheric or superatmospheric pressures.

The fluorinating agent may be chosen from the group consisting of hydrogen fluoride, cobalt fluoride, elemental fluorine or fluoride salts. Any of the known art catalysts and conditions may be used for the hydrofluorination in either the vapor phase (e.g., chromium oxide) or the liquid phase (e.g., antimony chloride).

The dehalogenation reaction of said compounds of the formula $C_mH_dCl_eF_f$ with hydrogen is typically conducted at a temperature from about 100° C. to 350° C., preferably from about 125° C. to 325° C., and more preferably from about 150° C. to about 300° C. Typically, the contact time is from about 1 to about 100 seconds, preferably from about 5 to about 60 seconds. The molar ratio of hydrogen to $C_mH_dCl_eF_f$ compound(s) ordinarily should be at least about 1:1. Typically, the molar ratio of hydrogen to said compounds of the formula $C_mH_dCl_eF_f$ ranges from about 1:1 to about 5:1, preferably about 1:1 to 3:1, and more preferably about 1:1 to 2:1. In general, with a given catalyst composition, the higher the temperature and the longer the contact time, the greater is the conversion to dehalogenated products. The above variables can be balanced, one against the other, so that the formation of dehalogenated products is maximized.

Examples of halogenated hydrocarbons of the formula $C_mH_dCl_eF_f$ which may be reacted with hydrogen include $CCl_3CClF_2$, $CCl_2FCClF_2$, $CClF_2CCl_2CF_3$, $CF_3CCl_2CF_3$, $CClF_2CClFCClF_2$, $CClF_2CF_2CClF_2$, $CClF_2CClFCF_3$ and $CCl_2FCF_2CF_3$. Of note is a catalytic process for producing 2-chloro-1,1,3,3,3-pentafluoropropene-1 (i.e., F1215xc or $CF_2=CCClF_3$) by the reaction of hydrogen with $CF_3CCl_2CF_3$. This dehalogenation reaction is done in the presence of the supported ruthenium catalysts described above and is preferably conducted at about 125° C. to 325° C., more preferably about 150° C. to 275° C.

Also of note is a catalytic process for producing 1,1-dichloro-2,2-difluoroethene (i.e., F1112a or $CF_2=CCl_2$). The starting material is 1,1,1,2-tetrachloro-2,2-difluoroethane.

The hydrofluorination reaction of said compounds of the formula $C_kH_gCl_hF_i$ with HF is typically conducted at a temperature of from about 150° C. to 400° C., preferably at from about 150° C. to 375° C., and more preferably at about 175° C. to about 350° C. Typically, the contact time is from about 1 to about 120 seconds, preferably from about 5 to about 60 seconds. The amount of HF ordinarily should be at least a stoichiometric amount. Typically, the molar ratio of HF to said compounds of the formula $C_kH_gCl_hF_i$ ranges from about 1:1 to about 20:1, preferably from about 2:1 to 10:1, and more preferably from about 3:1 to 6:1. In general, with a given catalyst composition, the higher the temperature and the longer the contact time, the greater is the conversion to fluorinated products. The above variables can be balanced, one against the other, so that the formation of higher fluorine substituted products is maximized.

An example of a saturated compound which may be reacted with HF includes $CCl_3CF_3$. Of note is a catalytic process for producing 2,2-dichloro-1,1,1,2-tetrafluoroethane ($CCl_2FCF_3$, i.e., CFC-114a) by the fluorination of $CCl_3CF_3$.

The hydrogenolysis reaction of said compounds of the formula $CF_3(CF_2)_pCCl_2(CF_2)_qCF_3$ with $H_2$ is typically conducted at a temperature of from about 100° C. to 350° C., preferably of from about 150° C. to 275° C., more preferably from about 150° C. to 250° C. Typically, the contact time is from about 1 to about 100 seconds, preferably from about 5 to about 60 seconds. Typically, the molar ratio of hydrogen to said compounds of the formula $CF_3(CF_2)_pCCl_2(CF_2)_qCF_3$ ranges from about 0.5:1 to 10:1 and is preferably from about 1:1 to 4:1. Of note is the monohydrogenolysis of $CF_3CCl_2CF_3$ to $CF_3CHClCF_3$ using ruthenium supported on barium fluoride.

The processes for dimerizing, dehalogenating, hydrofluorinating, and hydrogenolyzing halogenated hydrocarbons in accordance with this invention may be conducted in any suitable reactor, including fixed and fluidized bed reactors. The reaction vessel should be constructed from materials which are resistant to the corrosive effects of hydrogen fluoride and hydrogen chloride such as Inconel™ nickel alloy and Hastelloy™ nickel alloy.

Atmospheric and superatmospheric pressures are the most convenient and are therefore the preferred method of operation. The reaction products may be separated by conventional techniques such as distillation. It is noted that many halogenated hydrocarbon products of the above reactions form azeotropes with HF, HCl, or other halogenated hydrocarbons.

Examples of catalysts of this invention include ruthenium supported on zinc fluoride, magnesium fluoride, calcium fluoride, barium fluoride, yttrium fluoride, samarium fluoride, europium fluoride, or dysprosium fluoride. Also included are catalysts of ruthenium supported on fluorides of two or more metals selected from the group consisting of Zn, Mg, Ca, Ba, Y, Sm, Eu and Dy. Examples of such combined fluorides include calcium-magnesium fluoride where the atomic ratio of calcium to magnesium is between about 1:1 and 4:1; and calcium-barium fluoride where the atomic ratio of calcium to barium is between about 1:1 and 4:1. Typically, the ruthenium is from about 0.1 to 30 weight percent of the catalyst. Of note are compounds where the ruthenium is from about 0.5 to 20 weight percent of the catalyst.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLES

Ruthenium on Metal Fluoride Catalyst Preparation Procedure

Ruthenium Trichloride ($RuCl_3.xH_2O$) was dissolved in distilled water and added to a plastic beaker containing the metal fluoride. The weights of the ruthenium trichloride and the metal fluorides were selected to provide a catalyst containing 2 wt. % Ru on the support (see table). The slurry was kept at room temperature with occasional stirring for about 2 hours. The slurry was then dried at 110° C. to 120° C. overnight.

| Support (wt.) g | RuCl₃ (wt.) g | % Ru in RuCl₃.xH₂O |
|---|---|---|
| CaF₂ (200.0) | 9.52 | 42 |
| MgF₂ (200.0) | 11.29 | 35 |
| ZnF₂ (47.5) | 2.68 | 35 |
| YF₃ (80.0) | 3.80 | 42 |
| AlF₃ .3H₂O (100.0) | 3.47 | 41 |
| BaF₂ (100.0) | 4.80 | 41 |
| DyF₃ (100.0) | 4.80 | 41 |
| EuF₃ (48.0) | 2.30 | 41 |
| SmF₃ (75.0) | 3.60 | 41 |

5% Ru on Fluorided Alumina Catalyst Preparation

A commercially available sample of 5.0 weight percent ruthenium on alumina (12.22 g, 12/20 mesh (1.68 mm to 0.84 mm) granules) was placed in a reactor and heated to 175° C. in a flow of nitrogen (20 cc/min.) for about 2 hours. At the end of this period the nitrogen flow was increased to 50 cc/min. and an HF flow (50 cc/min.) was passed through the reactor. After the initial exotherm subsided (about three hours), the nitrogen flow was reduced to 20 cc/min. and the HF flow increased to 80 cc/min. The reactor temperature was then gradually increased to about 400° C. over about a five hour period and maintained at 400° C. for an additional 30 minutes. The HF flow was then stopped and the reactor purged with nitrogen and cooled to about 150° C. The catalyst was then treated with hydrogen (22 cc/min) at this temperature for about 0.5 hours followed by treatment with hydrogen (22 cc/min) for about another 0.5 hours at 175° C. before use.

General Procedure for Catalyst Evaluation

For the examples using metal fluoride as the support, the granulated catalyst (12/20 mesh, 1.68 mm to 0.84 mm) was placed in a ½" (1.27 cm) Inconel™ nickel alloy reactor heated in a fluidized sand bath. The catalyst was heated to about 200° C. in a flow of nitrogen (50 cc/min) for about two hours. After this period, it was heated in a stream of hydrogen (50 cc/min) for about 2 hours at about 200° C. prior to evaluation. Liquid feeds were delivered using a metering pump and were vaporized and mixed with either HF or hydrogen prior to entering the reactor. Vapor feeds were delivered using standard mass flow meters.

General Procedure for Product Analysis

The following general procedure is illustrative of the analytical method used. Part of the total reactor effluent was sampled on-line for organic product analysis using a Hewlett Packard HP 5890 gas chromatograph equipped with a 20' (6.1 m) long×⅛" (0.32 cm) diameter tubing containing Krytox™ perfluorinated polyether on an inert carbon support. The helium flow was 35 cc/min. Gas chromatographic conditions were 70° C. for an initial hold period of three minutes followed by temperature programming to 180° C. at a rate of 6° C./minute. Positive product identification including determination of molecular formulas of compounds of undetermined structure was obtained using mass spectroscopy.

The bulk of the reactor effluent containing organic products and also inorganic acids such as HCl and HF was treated with aqueous caustic to neutralize the acids prior to disposal.

Legend

F11 is $CFCl_3$
F113 is $CF_2ClCFCl_2$
F114a is $CF_3CFCl_2$
F122 is $CHCl_2CClF_2$
F124 is $CF_3CFHCl$
F134a is $CF_3CH_2F$
F143a is $CH_3CF_3$
F215cb is $CCl_3CF_2CF_3$
F216aa is $CF_3CCl_2CF_3$
F217ba is $CF_3CClFCF_3$
F236fa is $CF_3CH_2CF_3$
F356mff is $CF_3CH_2CH2CF_3$
TCE is $CHCl=CCl_2$
F1111 is $C_3Cl_5F$
F1132a is $CF_2=CH_2$
F1214 is $C_3Cl_2F_4$
F1216 is $CF_3CF=CF_2$
F1224 is $C_3HClF_4$
F1326 is $C_4HClF_6$
F1314 is cis/trans isomers of $CF_2ClCCl=CClCF_2Cl$
F318 is isomers of $C_4Cl_2F_8$
F1316mxx is $CF_3CCl=CClCF_3$ (cis/trans isomers)
F1318 is cis/trans isomers of $CF_3CF=CFCF_3$
F151-10mcxx is $C_2F_5CCl=CClC_2F_5$(cis/trans isomers)
F151-12mmtt is $(CF_3)_2C=C(CF_3)_2$ F112a is $CF_2ClCCl_3$
F113a is $CF_3CCl_3$
F115 is $CF_3CF_2Cl$
F123 is $CF_3CHCl_2$
F133a is $CF_3CH_2Cl$
F142b is $CH_3CClF_2$
F215aa is $CF_2ClCCl_2CF_3$
F225ca is $CF_3CF_2CHCl_2$
F216ba is $CF_2ClCFClCF_3$
F226da is $CF_3CClHCF_3$
F245cb is $CH_3CF_2CF_3$
HFP is $CF_3CF=CF_2$
PCE is $CCl_2=CCl_2$
F1112a is $CF_2=CCl_2$
1213xa is $CF_3CCl=CCl_2$
F1215xc is $CF_3CCl=CF_2$
F1223 is $C_3HCl_2F_3$
F1225zc is $CF_3CH=CF_2$

Example 1

Reaction of F113a and Hydrogen

Catalyst: 5% Ru/Fluorided Alumina (12.22 g, 15 mL)

The catalyst was fluorided in the reactor prior to use according to the procedure described above. The H₂:F113a molar ratio was varied between 0.5:1 to 2.0:1 and the contact time was 20 seconds for all runs. Results in area % at various temperatures are shown in the table.

| Temp. °C. | Ratio H₂:F113a | F143a | F114a | F123 | F113a | t-F1316mxx | c-F1316mxx | Others |
|---|---|---|---|---|---|---|---|---|
| 175 | 0.5 | 6.1 | 0.6 | 1.7 | 62.2 | 19.5 | 9.4 | 0.7 |
| 175 | 1.0 | 16.3 | 0.6 | 4.1 | 36.3 | 27.9 | 13.4 | 1.5 |
| 175 | 2.0 | 29.7 | 0.6 | 6.9 | 15.0 | 30.7 | 14.4 | 2.8 |
| 200 | 0.5 | 3.9 | 0.6 | 1.2 | 59.9 | 22.2 | 11.6 | 0.7 |
| 290 | 1.0 | 11.6 | 0.6 | 4.0 | 27.0 | 36.6 | 18.9 | 1.4 |
| 200 | 2.0 | 20.1 | 0.6 | 6.5 | 7.2 | 41.9 | 21.3 | 2.4 |
| 225 | 2.0 | 16.3 | 0.7 | 6.9 | 1.0 | 46.1 | 26.0 | 3.2 |

Others include F1132a, F142b, F1112a, F133a, F113 and small quantities of unidentified products.

| Selectivity calculation for the above table | | | | |
|---|---|---|---|---|
| Temp. | Conv. | % Sel. to | | Combined Sel. to |
| ° C. | H₂:F113a | % | F143a | F1316mxx | F143a + F1316mxx |
| 175 | 0.5 | 37.8 | 16.1 | 76.6 | 92.7 |
| 175 | 1.0 | 63.7 | 25.6 | 64.8 | 90.4 |
| 175 | 2.0 | 85.0 | 34.9 | 53.0 | 87.9 |
| 200 | 0.5 | 40.1 | 9.7 | 84.3 | 94.0 |
| 200 | 1.0 | 73.0 | 15.9 | 76.0 | 91.9 |
| 200 | 2.0 | 92.8 | 21.7 | 68.1 | 89.8 |
| 225 | 2.0 | 99.0 | 16.4 | 72.8 | 89.2 |

Example 2

Reaction of F216aa and Hydrogen

Catalyst: 5% Ru/Fluorided Alumina (12.22 g 15 mL)

The catalyst was the same as that used in Example 1. The H₂:F216aa molar ratio was varied between 0.5:1 to 1.0:1 and the contact time was 20 seconds for all runs. Results in area % at various temperatures are shown in the table.

| Temp. ° C. | Ratio H₂:F216aa | F236fa | F1215xc | F226da | F216aa | F216ba | F151-12mmtt | Others |
|---|---|---|---|---|---|---|---|---|
| 200 | 1.0 | 3.7 | 1.1 | 14.4 | 66.3 | 1.1 | 12.8 | 0.6 |
| 200 | 0.5 | 2.2 | 0.7 | 8.5 | 76.3 | 1.1 | 10.8 | 0.4 |
| 250 | 0.5 | 3.2 | 1.6 | 10.0 | 59.3 | 1.1 | 24.2 | 0.6 |
| 300 | 0.5 | 0.9 | 0.8 | 7.0 | 55.9 | 1.1 | 32.0 | 2.4 |
| 300 | 1.0 | 2.3 | 2.4 | 16.7 | 24.3 | 1.2 | 50.7 | 2.5 |

Others include F1216, 1225zc, and unidentified products.

| Selectivity data for the above table | | | |
|---|---|---|---|
| | % Sel. to | | |
| % F216aa Conv. | F226da | F151-12mmtt | F226da + F151-12mmtt |
| 33.7 | 42.7 | 38.0 | 80.7 |
| 23.7 | 35.9 | 45.6 | 81.5 |
| 40.7 | 24.5 | 59.4 | 83.9 |
| 44.1 | 15.9 | 72.6 | 88.5 |
| 75.7 | 22.1 | 67.0 | 89.1 |

Example 3

Reaction of F216aa and Hydrogen

Catalyst: 2% Ru/AlF₃, 8.7 g, 10 mL

The H₂:F216aa molar ratio was varied between 0.5:1 to 1.0:1 and the contact time was 20 seconds for all runs.

Results in area % at various temperatures are shown in the table.

| Temp. ° C. | Ratio H₂:F216aa | F236fa | F1215xc | F226da | F216aa | F51-12mmtt | F1213xa | Others |
|---|---|---|---|---|---|---|---|---|
| 175 | 1.0 | 5.0 | 3.5 | 5.3 | 76.6 | 8.1 | 0.0 | 1.6 |
| 200 | 1.0 | 6.3 | 5.4 | 7.4 | 63.4 | 15.3 | 0.0 | 2.2 |
| 200 | 0.5 | 3.3 | 3.1 | 4.3 | 74.7 | 13.4 | 0.0 | 1.2 |
| 250 | 0.5 | 2.3 | 3.4 | 7.2 | 57.0 | 29.0 | 0.0 | 1.1 |
| 300 | 0.5 | 0.7 | 0.2 | 7.6 | 58.5 | 28.5 | 2.8 | 1.8 |
| 300 | 1.0 | 2.3 | 1.7 | 21.6 | 19.6 | 47.2 | 3.1 | 4.5 |

Others include CH₄, F1225zc, F217ba, C₆F₁₀, C₆HF₁₁, F1223, TCE and C₆H₂F₁₂.

Example 4

Reaction of F113a and Hydrogen

Catalyst: 2% Ru/AlF₃, 8.7 g, 10 mL

The H₂:F113a molar ratio was varied between 0.5:1 to 1.0:1 and the contact time was 20 seconds for all runs.

Results in area % at various temperatures are shown in the table.

| Temp. °C. | Ratio $H_2$:F113a | F143a | F114a | F1112a | F123 | F113 | F113a | t-F1316 | c-F1316 | Others |
|---|---|---|---|---|---|---|---|---|---|---|
| 175 | 1.0 | 1.8 | 0.7 | 0.7 | 2.6 | 0.3 | 32.4 | 39.3 | 21.9 | 0.3 |
| 175 | 2.0 | 3.3 | 0.8 | 0.8 | 2.7 | 0.3 | 20.2 | 45.9 | 25.5 | 0.5 |
| 175 | 0.5 | 0.6 | 0.5 | 0.4 | 1.1 | 0.3 | 59.5 | 23.9 | 13.7 | 0.1 |
| 200 | 0.5 | 0.7 | 0.7 | 0.4 | 1.1 | 0.3 | 53.6 | 26.8 | 16.4 | 0.2 |
| 200 | 1.0 | 1.5 | 0.9 | 0.9 | 2.2 | 0.3 | 27.2 | 41.4 | 25.0 | 0.4 |

Example 5

Reaction of F113a/$CCl_4$ (1:1) and Hydrogen

Catalyst: 2% Ru/$AlF_3$, 8.7 g, 10 mL

The $H_2$:[F113a:$CCl_4$] molar ratio was varied between 1:1 to 2:1 and the contact time was 20 seconds for all runs. Results in area % at various temperatures are shown in the next two tables.

| Temp. °C. | Ratio $H_2$:[113a:$CCl_4$] | $CH_4$ | $C_2H_6$ | F143a | F12 | F114a | F11 | F1112a | F123 | $CHCl_3$ |
|---|---|---|---|---|---|---|---|---|---|---|
| 175 | 1 | 0.1 | 0.0 | 0.0 | 0.0 | 0.1 | 0.2 | 0.4 | 0.2 | 1.4 |
| 175 | 2 | 0.3 | 0.1 | 0.1 | 0.0 | 0.1 | 0.2 | 0.6 | 0.3 | 1.2 |
| 200 | 2 | 0.7 | 0.2 | 0.4 | 0.0 | 0.4 | 0.2 | 1.6 | 1.4 | 0.5 |
| 250 | 2 | 2.9 | 0.8 | 2.4 | 0.3 | 2.4 | 0.2 | 7.7 | 6.0 | 0.0 |
| 250 | 1 | 1.0 | 0.1 | 0.1 | 0.6 | 0.5 | 1.2 | 11.1 | 1.3 | 0.9 |

| Temp. °C. | F113 | F113a | CCl4 | F1111 | t-F1316 | c-F1316 | F1213xa | PCE | $C_4Cl_6$ | Others |
|---|---|---|---|---|---|---|---|---|---|---|
| 175 | 0.2 | 65.1 | 0.5 | 0.0 | 0.5 | 0.3 | 3.9 | 26.8 | 0.0 | 0.3 |
| 175 | 0.2 | 62.3 | 0.2 | 0.0 | 0.8 | 0.5 | 3.8 | 28.9 | 0.0 | 0.4 |
| 200 | 0.2 | 47.1 | 0.2 | 0.0 | 7.1 | 4.6 | 4.8 | 29.7 | 0.0 | 0.9 |
| 250 | 0.3 | 5.1 | 0.0 | 0.3 | 21.9 | 15.0 | 7.9 | 21.6 | 2.3 | 3.1 |
| 250 | 0.2 | 53.7 | 0.4 | 0.4 | 2.7 | 1.9 | 3.6 | 16.4 | 1.6 | 2.2 |

Example 6

Reaction of F113a and Hydrogen

Catalyst: 2% Ru/$ZnF_2$, 16.4 g, 10 mL

The $H_2$:F113a molar ratio was varied between 0.5:1 to 2:1 and the contact time was 20 seconds for all runs. Results in area % at various temperatures are shown in the table.

| Temp. °C. | Ratio $H_2$:F113a | F143a | F114a | F123 | F113 | F113a | t-F1316 | c-F1316 | Others |
|---|---|---|---|---|---|---|---|---|---|
| 175 | 1.0 | 0.6 | 0.2 | 1.0 | 0.3 | 47.2 | 33.4 | 16.9 | 0.4 |
| 175 | 2.0 | 1.5 | 0.2 | 1.4 | 0.3 | 31.2 | 43.6 | 21.4 | 0.4 |
| 200 | 2.0 | 2.2 | 0.3 | 2.4 | 0.4 | 9.0 | 54.7 | 30.2 | 0.9 |
| 200 | 1.0 | 0.8 | 0.3 | 1.9 | 0.4 | 22.7 | 46.5 | 26.9 | 0.5 |
| 200 | 0.5 | 0.2 | 0.2 | 0.8 | 0.3 | 51.7 | 29.0 | 17.5 | 0.2 |

Example 7

Reaction of F216aa and Hydrogen

Catalyst: 2% $Ru/ZnF_2$, 16.4 g, 10 mL

The $H_2$:F216aa molar ratio was varied between 0.5:1 to 2:1 and the contact time was 20 seconds for all runs. Results in area % at various temperatures are shown in the table.

| Temp. °C. | Ratio $H_2$:F216aa | F1225zc | F236fa | F1215xc | F226da | F216aa | F151-12mtt | Others |
|---|---|---|---|---|---|---|---|---|
| 200 | 1.0 | 0.0 | 0.2 | 0.0 | 0.7 | 84.3 | 14.4 | 0.3 |
| 250 | 1.0 | 0.1 | 0.4 | 0.2 | 3.7 | 42.7 | 50.1 | 2.7 |
| 250 | 0.5 | 0.0 | 0.1 | 0.1 | 2.5 | 69.0 | 25.4 | 2.8 |
| 300 | 0.5 | 0.2 | 0.2 | 1.3 | 3.3 | 71.3 | 14.1 | 9.7 |
| 300 | 1.0 | 0.3 | 0.3 | 1.7 | 4.0 | 73.9 | 6.6 | 13.3 |

Example 8

Reaction of F113a and Hydrogen

Catalyst: 2% $Ru/MgF_2$, 13.5 g, 15 mL

The $H_2$:F114a molar ratio was varied between 1:1 and 4:1, the contact time was 20 seconds and the temperature was 175° C. for all runs. Results in area % are shown in the table.

| Ratio $H_2$:F113a | F143a | F114a | F123 | F113a | t-F1316mxx | c-F1316mxx | Others |
|---|---|---|---|---|---|---|---|
| 1 | 2.5 | 0.8 | 3.1 | 33.3 | 40.0 | 19.6 | 0.8 |
| 1 | 2.4 | 0.7 | 2.8 | 33.5 | 40.1 | 19.8 | 0.7 |
| 1 | 2.2 | 0.7 | 2.6 | 34.8 | 39.4 | 19.5 | 0.7 |
| 2 | 5.2 | 0.7 | 3.6 | 18.3 | 48.0 | 23.3 | 0.9 |
| 4 | 10.5 | 0.8 | 4.5 | 7.4 | 51.2 | 24.3 | 1.3 |

Example 9

Reaction of F216aa and Hydrogen

Catalyst: 2% $Ru/MgF_2$, 13.5 g, 15 mL

The $H_2$:F216aa molar ratio was varied between 1:1 and 2:1 and the contact time was 20 seconds. Results in area % at various temperatures are shown in the table.

| Temp. °C. | Ratio $H_2$:F216aa | F1225zc | F236fa | F1215xc | F226da | F216aa | F151-12mmtt | Others |
|---|---|---|---|---|---|---|---|---|
| 175 | 1 | 0.2 | 2.8 | 9.8 | 3.8 | 77.6 | 5.1 | 0.7 |
| 175 | 2 | 0.3 | 4.6 | 13.8 | 4.7 | 70.1 | 5.8 | 0.8 |
| 200 | 1 | 0.3 | 3.1 | 20.9 | 4.4 | 62.2 | 8.1 | 0.9 |
| 250 | 1 | 0.9 | 4.0 | 54.7 | 8.4 | 20.1 | 10.8 | 1.1 |
| 300 | 1 | 0.6 | 2.4 | 67.9 | 10.1 | 5.0. | 11.4 | 2.7 |
| 300 | 2 | 2.0 | 4.3 | 65.3 | 11.2 | 0.0 | 13.3 | 3.9 |

Example 10

Reaction of F215cb and Hydrogen

Catalyst: 2% Ru/MgF$_2$, 13.5 g, 15 mL

The H$_2$:F215cb molar ratio was varied between 1:1 and 2:1 and the contact time was 20 seconds. The feed was 95.3% 215cb, 2.3% CCl$_4$ and small amounts of other products. Results in area % at 150° C. are shown in the table.

| Temp. °C. | Ratio H$_2$:215cb | F215cb | PCE | F151-10mcxx | C$_4$F$_5$Cl$_3$ | F151-10mcxx | Others |
|---|---|---|---|---|---|---|---|
| 150 | 2 | 17.8 | 3.1 | 68.9 | NA | 6.7 | 3.5 |
| 150 | 1 | 44.1 | 3.1 | 31.1 | 15.3 | 2.9 | 3.4 |

Others include 225ca, 245cb, and small amounts of unidentified products. NA means not analyzed.

Example 11

Reaction of F215cb and Hydrogen

Catalyst: 2% Ru/CaF$_2$, 10.5 g, 10 mL

The H$_2$:F215cb molar ratio was varied between 1:1 and 2:1 and the contact time was 20 seconds. The feed material contained 95.3% F215cb, 2.3% CCl$_4$ and small amounts of other products. Results in area % at various temperatures are shown in the table.

| Temp. °C. | Ratio H$_2$:215cb | F215aa | F215cb | PCE | F151-10mcxx | C$_4$F$_5$Cl$_3$ | F151-10mcxx |
|---|---|---|---|---|---|---|---|
| 150 | 1 | 1.5 | 38.6 | 3.3 | 37.1 | 11.2 | 5.4 |
| 150 | 2 | 1.2 | 27.8 | 3.4 | 46.2 | 10.5 | 6.6 |
| 175 | 1 | 1.3 | 28.2 | 3.9 | 46.7 | 9.6 | 6.7 |
| 200 | 1 | 0.8 | 17.5 | 4.0 | 55.4 | 8.2 | 9.1 |
| 225 | 1 | 0.7 | 15.9 | 3.8 | 53.7 | 10.3 | 9.8 |

Small amounts of other products were present.

Example 12

Reaction of F113a and Hydrogen

Catalyst: 2% Ru/CaF$_2$, 10.5 g, 10 mL

The H$_2$: F113a molar ratio was varied between 1:1 and 4:1, the reaction temperature was 175° C. and the contact time was 20 seconds. Results in area % are shown in the table.

| Ratio H$_2$:F113a | F143a | F114a | F123 | F113a | t-F1316mxx | c-F1316mxx | Others |
|---|---|---|---|---|---|---|---|
| 1 | 3.1 | 0.6 | 1.4 | 63.3 | 17.7 | 13.4 | 0.5 |
| 2 | 5.6 | 0.6 | 2.0 | 51.1 | 23.6 | 16.6 | 0.7 |
| 4 | 8.9 | 0.6 | 2.7 | 39.4 | 29.0 | 18.3 | 1.1 |

Others include $CH_4$, F142b, F1132a, F1326, and F113.

Example 13

Reaction of F216aa and Hydrogen

Catalyst: 2% $Ru/CaF_2$, 10.5 g, 10 mL

The $H_2$:F216aa molar ratio was varied between 1:1 and 2:1 and the contact time was 20 seconds. Results in area % at various temperatures are shown in the table.

| Temp. °C. | Ratio $H_2$:F216aa | F1225zc | F236fa | F1215xc | F226da | F216aa | F151-12mmtt | Others |
|---|---|---|---|---|---|---|---|---|
| 175 | 1 | 0.0 | 0.7 | 0.3 | 0.5 | 94.5 | 4.0 | 0.1 |
| 200 | 1 | 0.1 | 1.4 | 0.7 | 1.2 | 87.6 | 8.9 | 0.1 |
| 225 | 1 | 0.1 | 1.8 | 1.3 | 2.6 | 77.5 | 16.3 | 0.3 |
| 250 | 1 | 0.2 | 2.1 | 2.6 | 5.4 | 62.3 | 26.7 | 0.7 |
| 275 | 1 | 0.6 | 2.3 | 4.9 | 11.5 | 41.8 | 37.9 | 1.1 |
| 275 | 2 | 0.8 | 3.6 | 6.8 | 14.9 | 26.5 | 45.7 | 1.7 |
| 300 | 1 | 0.8 | 1.9 | 7.1 | 17.8 | 26.5 | 44.3 | 1.6 |

Example 14

Reaction of F113a and Hydrogen

Catalyst: 2% $Ru/BaF_2$, 24.4 g, 10 mL

The $H_2$:113a molar ratio was 1 and the contact time was 20 seconds. Results in area % at 175° C. showed the presence of the following compounds: F143a, 2.0; F114a, 0.3; F123, 7.0; F1326, 0.4; F113a, 26.5; t-F1316, 41.4; c-F1316, 21.5 and 0.9 others. Others include F1132a and F113.

Example 15

Reaction of F216aa and Hydrogen

Catalyst: 2% $Ru/BaF_2$, 24.4 g, 10 mL

The $H_2$:F216aa molar ratio was varied between 0.5:1 and 1:1 and the contact time was 20 seconds. Results in area % at various temperatures are shown in the table.

| Temp. °C. | Ratio $H_2$:F216aa | F236fa | F1215xc | F226da | F216aa | $C_6F_{10}$ | F151-12mmtt | Others |
|---|---|---|---|---|---|---|---|---|
| 200 | 1.0 | 0.6 | 40.0 | 33.3 | 23.7 | 0.7 | 1.3 | 0.4 |
| 200 | 0.5 | 0.4 | 27.6 | 19.2 | 50.6 | 0.7 | 1.2 | 0.3 |
| 250 | 0.5 | 0.4 | 35.8 | 6.7 | 53.3 | 1.2 | 2.3 | 0.3 |

Others include F1225zc and $C_6HF_{11}$.

Example 16

Reaction of F216aa and Hydrogen

Catalyst: 2% $Ru/YF_3$, 16.5 g, 10 mL

The $H_2$:F216aa molar ratio was varied between 0.5:1 and 1:1 and the contact time was 20 seconds. Results in area % at various temperatures are shown in the table.

| Temp. °C. | Ratio $H_2$:F216aa | F236fa | F1215xc | F226da | F216aa | $C_6F_{10}$ | $C_6F_{12}$ | Others |
|---|---|---|---|---|---|---|---|---|
| 175 | 1.0 | 2.4 | 19.1 | 7.1 | 64.7 | 1.4 | 4.4 | 0.9 |
| 175 | 0.5 | 1.5 | 10.0 | 4.1 | 78.5 | 1.1 | 4.2 | 0.6 |
| 200 | 0.5 | 1.8 | 13.7 | 4.3 | 69.9 | 2.0 | 7.4 | 0.9 |
| 250 | 0.5 | 0.4 | 2.5 | 4.3 | 64.2 | 0.3 | 27.0 | 1.4 |
| 250 | 1.0 | 0.6 | 3.7 | 6.2 | 52.8 | 0.3 | 35.6 | 0.9 |
| 275 | 1.0 | 0.8 | 7.0 | 11.5 | 36.5 | 0.4 | 41.7 | 2.2 |
| 275 | 0.5 | 0.5 | 4.0 | 7.6 | 54.5 | 0.2 | 30.1 | 3.1 |
| 300 | 0.5 | 0.6 | 5.5 | 9.2 | 51.8 | 0.1 | 27.2 | 5.6 |
| 300 | 1.0 | 1.2 | 13.0 | 22.3 | 18.2 | 0.4 | 43.0 | 1.9 |

Others include $C_6F_{12}Cl_2$.

Example 17

Reaction of F112a and Hydrogen

Catalyst: 2% Ru/YF$_3$, 16.5 g 10 mL

The $H_2$:F112a molar ratio was varied between 0.5:1 and 1:1 and the contact time was 20 seconds. Results in area % at various temperatures are shown in the table.

| Temp. °C. | Ratio $H_2$:112a | F1112a | F122 | $C_4F_4Cl_2$ | $C_4F_4Cl_2$ | F112a | F1314 | F1314 | Others |
|---|---|---|---|---|---|---|---|---|---|
| 175 | 1.0 | 12.1 | 3.8 | 0.6 | 0.0 | 72.5 | 8.7 | 2.0 | 0.3 |
| 200 | 1.0 | 20.7 | 7.5 | 1.6 | 0.0 | 52.1 | 13.6 | 3.5 | 1.1 |
| 250 | 1.0 | 35.5 | 15.6 | 6.1 | 0.1 | 18.8 | 16.1 | 5.0 | 2.8 |
| 250 | 0.5 | 27.4 | 15.2 | 2.6 | 0.1 | 35.8 | 12.7 | 3.8 | 2.6 |
| 300 | 0.5 | 39.1 | 11.9 | 2.2 | 0.3 | 31.0 | 9.5 | 3.2 | 2.8 |
| 300 | 1.0 | 57.2 | 14.9 | 9.7 | 1.2 | 3.8 | 6.6 | 2.6 | 4.1 |

Example 18

Reaction of F114a and Hydrogen

Catalyst: 2% Ru/YF$_3$, 16.5 g, 10 mL

The $H_2$:F114a molar ratio was 2:1, the temperature was 350° C. and the contact time was 20 seconds. The products in area % were CH$_4$, 5.4, F143a, 4.1; F134a, 0.6; F124, 31.0; F1318, 3.0; F114a, 29.6; F1318, 3.0; F1112a, 1.7; F318, 3.4; F318, 3.9 $C_6Cl_2F_{10}$, 1.5; and others, 9.0.

Example 19

Reaction of F113a and Hydrogen

Catalyst: 2%Ru/SmF$_3$, 20.6 g, 10 mL

The $H_2$:F113a molar ratio was 1 and the contact time was 20 seconds. Results in area % at 175° C. showed the presence of the following compounds: F143a, 3.8; F142b, 0.4; F123, 4.6; F113, 0.4; F113a, 24.6; t-F1316, 43.8; c-F1316, 21.7 and 1.0 others. Others include $C_2H_6$, F133a and F114a.

Example 20

Reaction of F216aa and Hydrogen

Catalyst: 2% Ru/SmF$_3$, 20.6 g, 10 mL

The $H_2$:F216aa molar ratio was varied between 0.5:1 and 2:1 and the contact time was 20 seconds. Results in area % at various temperatures are shown in the table.

| Temp. °C. | Ratio $H_2$:F216aa | HFP | F236fa | F1215xc | F226da | F216aa | $C_6F_{12}$ | Others |
|---|---|---|---|---|---|---|---|---|
| 200 | 1.0 | 1.0 | 5.4 | 4.3 | 6.2 | 64.9 | 16.1 | 2.1 |
| 200 | 2.0 | 1.1 | 11.3 | 9.9 | 10.1 | 46.1 | 19.2 | 2.4 |
| 225 | 2.0 | 1.0 | 14.4 | 16.9 | 16.1 | 22.2 | 25.8 | 3.8 |
| 225 | 1.0 | 0.9 | 9.1 | 13.1 | 12.1 | 37.6 | 24.2 | 3.0 |
| 250 | 1.0 | 1.0 | 6.2 | 19.4 | 16.9 | 24.6 | 28.1 | 3.8 |
| 250 | 2.0 | 1.0 | 13.9 | 26.4 | 20.6 | 1.2 | 31.2 | 5.7 |
| 250 | 0.5 | 0.9 | 1.8 | 9.1 | 7.8 | 55.2 | 23.1 | 2.2 |

Others include CH$_4$, C$_2$H$_6$, C$_3$H$_8$, F1224, C$_6$HF$_{11}$, C$_5$F$_9$Cl, F1223, F1214, C$_6$F$_{10}$, F1225zc and C$_6$F$_{13}$Cl.

Example 21

Fluorination of F113a

Catalyst: 2% Ru/SmF$_3$, 20.6 g, 10 mL

The HF:F113a molar ratio was 2:1 and the contact time was 20 seconds. Results in mole % at various temperatures are shown in the table.

| Temp. °C. | F13 | F115 | F114a | F113 | F113a | Others |
|---|---|---|---|---|---|---|
| 250 | 0.0 | 0.0 | 1.1 | 0.3 | 98.5 | 0.1 |
| 275 | 0.0 | 0.0 | 3.0 | 0.3 | 96.4 | 0.3 |
| 325 | 0.3 | 0.0 | 14.4 | 0.3 | 84.7 | 0.3 |
| 350 | 0.3 | 0.1 | 22.1 | 0.3 | 77.0 | 0.2 |

Example 22

Reaction of F216aa and Hydrogen

Catalyst: 2% Ru/EuF$_3$, 19.1 g, 10 mL

The H$_2$:F216aa molar ratio was varied between 0.5:1 and 1:1 and the contact time was 20 seconds. Results in area % at various temperatures are shown in the table.

| Temp. °C. | Ratio H$_2$:F216aa | F236fa | F1215xc | F226da | F216aa | C$_6$F$_{10}$ | F151-12mmtt | Others |
|---|---|---|---|---|---|---|---|---|
| 175 | 1.0 | 2.4 | 21.2 | 5.5 | 60.8 | 2.3 | 7.3 | 0.7 |
| 176 | 0.5 | 1.2 | 12.4 | 3.2 | 74.9 | 1.7 | 6.1 | 0.4 |
| 200 | 0.5 | 1.0 | 7.5 | 3.4 | 72.8 | 0.8 | 14.2 | 0.4 |

Others include F1225zc, F1214, and C$_6$HF$_{11}$.

Example 23

Reaction of F113a and Hydrogen

Catalyst: 2% Ru/EuF$_3$, 19.1 g, 10 mL

The H$_2$:F113a molar ratio was 1 and the contact time was 20 seconds. Results in area % at 175° C. showed the presence of the following compounds: F143a, 2.0; F114a, 0.3; F123, 6.9; F113, 0.3; F113a, 22.0; t-F1316, 44.7; c-F1316, 23.0 and 0.7 others. Others include F1132a, F142b, F133a and F1112a.

Example 24

Fluorination of F113a

Catalyst: 2% Ru/EuF$_3$, 19.1 g, 10 mL

The HF:F113a molar ratio was 2:1 and the contact time was 20 seconds. Results in mole % at various temperatures are shown in the table.

| Temp. °C. | F115 | F114a | F123 | F113 | F113a | t-F1326 | C-F1326 | Others |
|---|---|---|---|---|---|---|---|---|
| 200 | 0.0 | 0.3 | 0.1 | 0.3 | 98.3 | 0.6 | 0.4 | 0.1 |
| 250 | 0.0 | 0.4 | 0.1 | 0.3 | 98.1 | 0.6 | 0.4 | 0.1 |
| 300 | 0.0 | 1.0 | 0.0 | 0.3 | 97.6 | 0.5 | 0.4 | 0.1 |
| 350 | 0.1 | 6.5 | 0.0 | 0.3 | 92.1 | 0.5 | 0.4 | 0.1 |

Example 25

Reaction of F113a and Hydrogen

Catalyst: 2% Ru/DyF$_3$, 21.1 g, 10 mL

The H$_2$:F113a molar ratio was 1 and the contact time was 20 seconds. Results in area % at 175° C. showed the presence of the following compounds: F143a, 2.3; F114a, 0.3; F123, 6.9; F113, 0.3; F113a, 27.5; t-F1316, 42.6; c-F1316, 19.9 and 0.4 others. Others include F1132a, F142b, F133a and F1112a.

Example 26

Reaction of F216aa and Hydrogen

Catalyst: 2% Ru/DyF$_3$, 21.1 g, 10 mL

The H$_2$:F216aa molar ratio was varied between 0.5:1 and 1:1 and the contact time was 20 seconds. Results in area % at various temperatures are shown in the table.

| Temp. °C | Ratio H$_2$:F216aa | F236fa | F1215xc | F226da | F216aa | C$_6$F$_{10}$ | F151-12mmtt | Others |
|---|---|---|---|---|---|---|---|---|
| 175 | 1.0 | 1.5 | 7.2 | 1.8 | 79.0 | 0.7 | 7.7 | 2.1 |
| 200 | 0.5 | 1.4 | 10.2 | 2.3 | 72.1 | 0.8 | 11.1 | 2.1 |
| 250 | 1.0 | 4.8 | 23.8 | 9.3 | 28.6 | 1.1 | 29.4 | 3.1 |

Example 27

Fluorination of F113a

Catalyst: 2% Ru/DyF$_3$, 21.1 g, 10 mL

The HF:F113a molar ratio was 2:1 and the contact time was 20 seconds. Results in mole % at various temperatures are shown in the table.

| Temp. °C | F114a | F113 | F113a | F1326 | F1326 | Others |
|---|---|---|---|---|---|---|
| 300 | 1.5 | 0.3 | 97.8 | 0.1 | 0.1 | 0.2 |
| 350 | 9.0 | 0.3 | 90.1 | 0.2 | 0.1 | 0.2 |

Catalyst Comparisons

Reaction of F216aa and Hydrogen

The table below, compares the performance of selected catalysts reported in the Examples above for the conversion of F216aa to F151-12mmtt at an operating temperature of 200° C., H$_2$/F216aa ratio of 0.5 and a contact time of 20 seconds. The data is from examples cited and the results are reported in area %. In this table, Catalyst 1 is 5% Ru on fluorided alumina, Catalyst 2 is 2% Ru on aluminum fluoride, Catalyst 3 is 2% Ru on dysprosium fluoride and Catalyst 4 is 2% Ru on europium fluoride.

| Catalyst | F236fa | F1215xc | F226da | F216aa | F151-12mmtt |
|---|---|---|---|---|---|
| 1 | 2.2 | 0.7 | 8.5 | 76,3 | 10.8 |
| 2 | 3.3 | 3.1 | 4.3 | 74.7 | 13.4 |
| 3 | 1.4 | 10.2 | 2.3 | 72.1 | 11.1 |
| 4 | 1.0 | 7.5 | 3.4 | 72.8 | 14.2 |

Catalyst Comparisons

Reaction of F216aa and Hydrogen

The following table compares selected data reported in the Examples above for the conversion of F216aa to F151-12mmtt, F1215xc and F226da at an operating temperature of 200° C., contact time of 20 seconds, and H$_2$/F216aa molar ratio of 1. In this table, Catalyst 1 is 2% Ru on magnesium fluoride, Catalyst 2 is 2% Ru on calcium fluoride and Catalyst 3 is 2% Ru on barium fluoride. Results are in area %.

| Catalyst | F236fa | F1215xc | F226da | F216aa | F151-12mmtt |
|---|---|---|---|---|---|
| 1 | 0.2 | 20.9 | 4.4 | 62.2 | 8.1 |
| 2 | 1.8 | 1.3 | 2.6 | 77.5 | 16.3 |
| 3 | 0.6 | 40.0 | 33.3 | 23.7 | 1.3 |

Catalyst Comparisons

Reaction of F113a and Hydrogen

The following table compares selected data from the Examples above on the reaction of F113a and hydrogen over various catalysts. In this table, all the supports had 2% ruthenium by weight. Reactor temperature was 175° C., contact time 20 seconds and the H$_2$/F113a ratio was 1. Results are in area %.

| Support | F143a | F123 | F113a | t-F1316 | c-F1316 | Others |
|---|---|---|---|---|---|---|
| SmF$_3$ | 3.9 | 4.4 | 25.1 | 43.5 | 21.6 | 1.5 |
| EuF3 | 1.9 | 6.7 | 22.6 | 44.3 | 23.2 | 1.3 |
| DyF$_3$ | 2.2 | 6.7 | 28.4 | 42.1 | 19.4 | 1.2 |

Others include F1132a, F142b, F133a, F112a and F114a.

I claim:

1. A process for decreasing the chlorine to carbon ratio for saturated or olefinic halogenated hydrocarbons containing chlorine and having the formula C$_k$H$_g$Cl$_h$F$_i$ where k is an integer from 1 to 6, g is an integer from 0 to 4, h is an integer from 1 to 13, and i is an integer from 0 to 13, in the presence of a catalyst, characterized by:

(a) employing a catalyst comprising ruthenium supported on a fluoride of at least one element selected from the group consisting of Zn, Mg, Ba, Y, Sm, Eu, and Dy; and (b) increasing the fluorine content of said halogenated hydrocarbons by reacting them with HF in the vapor phase.

2. The process of claim 1 wherein the catalyst consists essentially of ruthenium supported on zinc fluoride.

3. The process of claim 1 wherein the catalyst consists essentially of ruthenium supported on a fluoride of at least one element selected from the group consisting of Y, Sm, Eu and Dy.

4. The process of claim 1 wherein the catalyst comprises ruthenium supported on a calcium-magnesium fluoride where the atomic ratio of calcium to magnesium is between about 1:1 and 4:1.

5. The process of claim 1 wherein the catalyst comprises ruthenium supported on a calcium-barium fluoride where the atomic ratio of calcium to barium is between about 1:1 and 4:1.

6. A process for decreasing the chlorine to carbon ratio for a halogenated hydrocarbon containing two chlorine substituents on the same carbon atom and having the formula C$_n$H$_a$Cl$_b$F$_c$ where n is an integer from 1 to 4, a is an integer from 0 to 1, b is an integer from 2 to 9, c is an integer from 0 to 9, and a+b+c equals 2n+2, in the presence of a catalyst, characterized by:

(a) employing a catalyst comprising ruthenium on a support selected from the group consisting of (1) fluorided alumina, (ii) aluminum fluoride, and (iii) fluorides of at least one metal selected from the group consisting of Zn, Mg, Ca, Ba, Y, Sm, Eu, and Dy; and (b) reacting said halogenated hydrocarbon in the vapor phase to remove two chlorine substituents from the same carbon atom of said halogenated hydrocarbon and to produce a dimerized olefin of the formula $C_{2n}H_{2a}Cl_{2b-4}F_{2c}$.

7. A process for decreasing the chlorine to carbon ratio for halogenated hydrocarbons containing chlorine and having the formula $C_mH_dCl_eF_f$ where m is an integer from 2 to 6, d is an integer from 0 to 2, e is an integer from 2 to 4, f is an integer from 3 to 12, and d+e+f equals 2m+2, in the presence of a catalyst, characterized by:

dehalogenating said halogenated hydrocarbons in the presence of a catalyst comprising ruthenium on a support selected from the group consisting of (i) fluorided alumina, (ii) aluminum fluoride, and (iii) fluorides of at least one metal selected from the group consisting of Zn, Mg,,Ca, Ba, Y, Sm, Eu, and Dy, by reacting said compound with hydrogen in the vapor phase to produce an olefin of the formula $C_mH_dCl_{e-y}F_{f-y}$, where y is an integer from 1 to 2 when m is an integer from 2 to 3, and y is an integer from 2 to 4 when m is an integer from 4 to 6, provided that a chlorine atom on each of two adjacent carbons or a fluorine and a chlorine atom on two adjacent carbons, but not a fluorine atom on each of two adjacent carbons, are removed.

8. The process of claim 7 wherein $CF_3CCl_2CF_3$ is reacted with hydrogen to produce $CF_3CCl=CF_2$.

* * * * *